United States Patent
Harada et al.

(10) Patent No.: US 11,774,387 B2
(45) Date of Patent: Oct. 3, 2023

(54) WIRING STRUCTURE, CONDUCTIVE PARTICLE DETECTING DEVICE, AND SPEED REDUCER

(71) Applicant: Nabtesco Corporation, Tokyo (JP)

(72) Inventors: Masaki Harada, Tokyo (JP); Atsushi Koike, Tokyo (JP); Kazuhiko Sakurai, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 60 days.

(21) Appl. No.: 17/688,620

(22) Filed: Mar. 7, 2022

(65) Prior Publication Data
US 2022/0291159 A1    Sep. 15, 2022

(30) Foreign Application Priority Data
Mar. 12, 2021    (JP) .................. 2021-040414

(51) Int. Cl.
*G01N 27/07* (2006.01)
*H05K 1/02* (2006.01)
(Continued)

(52) U.S. Cl.
CPC ......... *G01N 27/07* (2013.01); *G01N 33/2858* (2013.01); *H05K 1/0277* (2013.01); *H05K 1/18* (2013.01); *H01F 7/02* (2013.01); *H05K 2201/10053* (2013.01); *H05K 2201/10151* (2013.01)

(58) Field of Classification Search
CPC .............. G01N 27/07; G01N 33/2858; G01N 15/0656; G01N 27/043; G01N 27/045; H05K 1/0277; H05K 1/18; H05K 2201/10053; H05K 2201/10151; H01F 7/02; F16H 57/0405
See application file for complete search history.

(56) References Cited

U.S. PATENT DOCUMENTS

| | | | |
|---|---|---|---|
| 2012/0105057 A1* | 5/2012 | Mol | G01D 5/145 324/251 |
| 2013/0050872 A1* | 2/2013 | Sekii | H02K 1/146 310/71 |

(Continued)

FOREIGN PATENT DOCUMENTS

| | | |
|---|---|---|
| EP | 0893683 A1 | 1/1999 |
| JP | 2005-331324 A | 12/2005 |
| WO | 2020/152175 A1 | 7/2020 |

OTHER PUBLICATIONS

Extended European Search Report dated Jul. 15, 2022, issued in corresponding European Patent Application No. 22160550.4 (9 pgs.).

*Primary Examiner* — Giovanni Astacio-Oquendo
*Assistant Examiner* — Zannatul Ferdous
(74) *Attorney, Agent, or Firm* — Pillsbury Winthrop Shaw Pittman, LLP

(57) ABSTRACT

A wiring structure includes a wiring such as a flexible printed wiring board, a permanent magnet, and a relay piece. The wiring has a conductive portion. The permanent magnet has electrical conductivity. The relay piece is formed of a conductive metal and connected to the conductive portion of the wiring. The relay piece has the permanent magnet fixed thereto by magnetic attraction.

6 Claims, 6 Drawing Sheets

(51) Int. Cl.
*H05K 1/18* (2006.01)
*G01N 33/28* (2006.01)
*H01F 7/02* (2006.01)

(56) References Cited

U.S. PATENT DOCUMENTS

2014/0021945 A1* 1/2014 Omoto ................. F16C 35/042
   324/207.25
2019/0154608 A1 5/2019 Nakamura et al.

* cited by examiner

WIRING STRUCTURE, CONDUCTIVE PARTICLE DETECTING DEVICE, AND SPEED REDUCER

CROSS-REFERENCE TO RELATED APPLICATIONS

This application is based on and claims the benefit of priority from Japanese Patent Application Serial No. 2021-040414 (filed on Mar. 12, 2021), the contents of which are hereby incorporated by reference in their entirety.

TECHNICAL FIELD

The present disclosure relates to a wiring structure, a conductive particle detecting device using the wiring structure, and a speed reducer using the conductive particle detecting device.

BACKGROUND

In apparatuses containing a mechanical mechanism (such as a speed reducer), a casing is filled with a lubricant to reduce the wear in the mechanism. In operation of such apparatuses, metal powder is produced from mechanical parts. The metal powder produced from the mechanical parts mixes into the lubricant within the casing. When a large amount of metal powder mixes into the lubricant, the ability of the lubricant to inhibit the wear in the mechanism is reduced. The presence of the large amount of metal powder mixed into the lubricant indicates that the wear or damage has occurred in the mechanism.

For the above apparatuses, a device should preferably externally detect that the amount of the metal powder in the lubricant has exceeded a preset value. Devices for externally detecting the amount of the metal powder are disclosed (see, for example, Japanese Patent Application Publication No. 2005-331324 ("the '324 Publication")). With these devices, the metal powder in the lubricant is attracted by a permanent magnet, thereby electrically detecting the amount of the attracted metal powder.

The detecting device (the conductive particle detecting device) disclosed in the '324 Publication includes a tubular permanent magnet disposed in the lubricant and a plurality of electrodes disposed outside the permanent magnet and spaced apart from each other by a gap.

The conductive particle detecting device is configured to detect the resistance between adjacent electrodes spaced apart from each other by the gap, thereby determining the amount of metal powder mixing into the lubricant.

Some conductive particle detecting devices proposed in recent years include a plurality of permanent magnets having electrical conductivity used as electrodes. In the conductive particle detecting devices, the permanent magnets serve as both attracting portions for conductive particles (such as metal powder) and electrode portions. Each of the permanent magnets is connected through wiring to a resistance detecting circuit on a detecting circuit board.

A wiring structure connecting between the detecting circuit board and the conductive permanent magnets includes a connecting means for connecting between a conductive portion of the wiring and a corresponding permanent magnet. The connecting means is formed of a screw or a conductive clamping lock.

When the connecting means is formed of a screw, the permanent magnet needs to have a screw hole formed therein. However, it is generally difficult to form a screw hole in a permanent magnet to a high accuracy. The clamping lock as the connecting means is a large-sized part. Therefore, use of the clamping lock as the connecting means causes increase of the size of the entire wiring structure.

SUMMARY

An aspect of the disclosure provides a wiring structure, a conductive particle detecting device, and a speed reducer, in which it is possible to easily connect between a conductive portion of the wiring and a conductive permanent magnet without an increase of the size of a connecting portion.

(1) A wiring structure according to one aspect of the present disclosure comprises: a permanent magnet having electrical conductivity; a wiring having a conductive portion; and a relay piece made of a metal magnetic material, the relay piece being connected to the conductive portion, the permanent magnet being fixed to the relay piece by magnetic attraction.

(2) The wiring is preferably formed of a flexible printed wiring board.

(3) The relay piece and the permanent magnet may be connected by a conductive adhesive.

(4) A conductive particle detecting device according to one aspect of the present disclosure comprises: a plurality of permanent magnets having electrical conductivity and spaced apart from each other; a detecting circuit board for detecting conductive particles attracted between adjacent ones of the plurality of permanent magnets, based on electrical resistance between the adjacent ones of the plurality of permanent magnets; a flexible printed wiring board electrically connecting the detecting circuit board and the plurality of permanent magnets; and a plurality of relay pieces connected to conductive portions of the flexible printed wiring board. The plurality of relay pieces are made of a metal magnetic material. The plurality of permanent magnets are fixed to the plurality of relay pieces, respectively, by magnetic attraction.

(5) The conductive portions and the plurality of relay pieces may be connected by solder.

(6) The conductive portions and the plurality of relay pieces may be connected by a conductive adhesive.

(7) The conductive particle detecting device may further comprise: a sealing member sealing between a lubricant-filled space containing the plurality of permanent magnets and filled with a lubricant and a detection space containing the detecting circuit board. The sealing member may be integrated with the flexible printed wiring board.

(8) A speed reducer according to one aspect of the present disclosure comprises: a speed reducing mechanism unit for reducing a speed of rotation input thereto; a casing containing the speed reducing mechanism unit; and a conductive particle detecting device for detecting conductive particles mixing into a lubricant in the casing. The conductive particle detecting device includes: a plurality of permanent magnets having electrical conductivity and spaced apart from each other within the casing; a detecting circuit board for detecting conductive particles attracted between adjacent ones of the plurality of permanent magnets, based on electrical resistance between the adjacent ones of the plurality of permanent magnets; a flexible printed wiring board electrically connecting the detecting circuit board and the plurality of permanent magnets; and a plurality of relay pieces connected to conductive portions of the flexible printed wiring board. The plurality of relay pieces are made of a metal magnetic material. The plurality of permanent magnets are fixed to the plurality of relay pieces, respectively, by magnetic attraction.

The above wiring structure includes the relay piece made of a metal magnetic material and connected to the conductive portion of the wiring, and the permanent magnet is fixed to the relay piece by magnetic attraction. Therefore, in connecting the conductive portion of the wiring and the permanent magnet having electrical conductivity, there is no need of a cutting process for forming a screw hole or the like in the permanent magnet. Accordingly, with the above wiring structure, it is possible to easily connect the conductive portion of the wiring and the permanent magnet having electrical conductivity without increase of the size of the connection portion.

DESCRIPTION OF THE EMBODIMENTS

The embodiments of the present disclosure will be hereinafter described with reference to the drawings. In the following embodiments, like elements will be denoted by the same reference signs and redundant descriptions will be partly omitted.

First Embodiment

Figure 1:
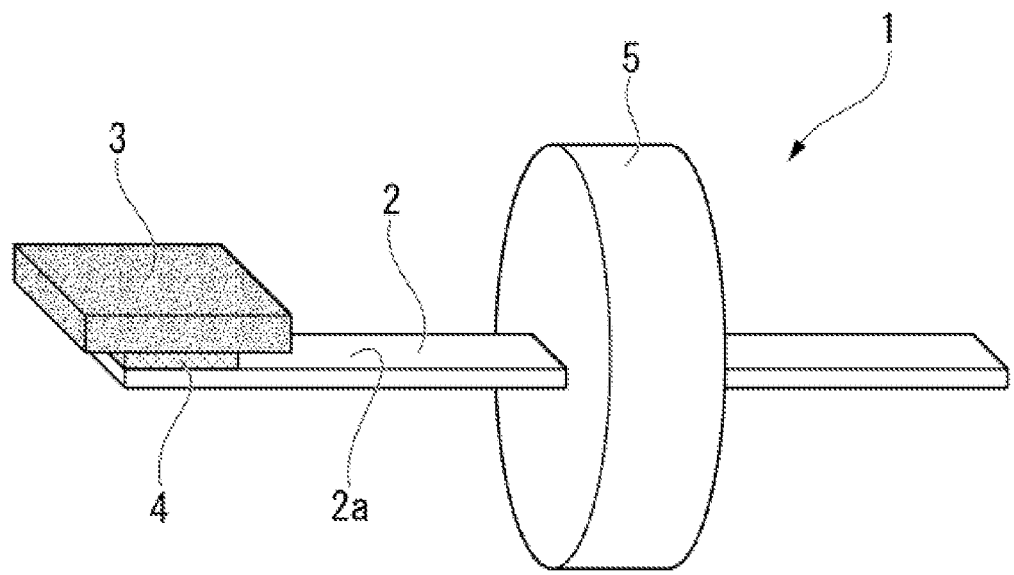
FIG. 1 is a perspective view showing a wiring structure according to a first embodiment.

FIG. 1 is a perspective view showing a wiring structure 1 according to a first embodiment. The wiring structure 1 of the embodiment includes a permanent magnet 3 having electrical conductivity, a flexible printed wiring board (a form of wiring) 2, and a relay piece 4 formed of a metal magnetic material.

The permanent magnet 3 is shaped like a rectangular plate with some degree of thickness. The flexible printed wiring board 2 is shaped like a belt. The flexible printed wiring board 2 includes a conductive portion (not shown) extending from one end of the flexible printed wiring board 2 toward the other end in the longitudinal direction. The conductive portion is covered by an insulating layer 2a having flexibility. One end portion and the other end portion of the conductive portion form a terminal portion (not shown) exposed to the outside of the insulating layer 2a.

The relay piece 4 is soldered to one end portion of the terminal portion. Thus, the relay piece 4 is electrically connected to the conductive portion of the flexible printed wiring board 2. The relay piece 4 is formed of a magnetic material such as a metal. The permanent magnet 3 can be attached to the relay piece 4 by magnetic attraction. The relay piece 4 is shaped like a rectangular plate having substantially the same width as the flexible printed wiring board 2. The top and bottom surfaces (the surfaces facing toward the thickness direction) of the relay piece 4 are flat. In the embodiment, the relay piece 4 is soldered to the terminal portion (the conductive portion) of the flexible printed wiring board 2. It is also possible to use a conductive adhesive to connect the relay piece 4 to the terminal portion (the conductive portion) of the flexible printed wiring board 2. In this case, the conductive adhesive electrically connects between the relay piece 4 and the terminal portion of the flexible printed wiring board 2. Since the relay piece 4 is shaped like a rectangular plate having substantially the same width as the flexible printed wiring board 2, the relay piece 4 and the flexible printed wiring board 2 can be fixed with an adhesive to each other at the surfaces thereof facing the thickness direction, such that the relay piece 4 is stably fixed to the flexible printed wiring board 2.

Figure 2:
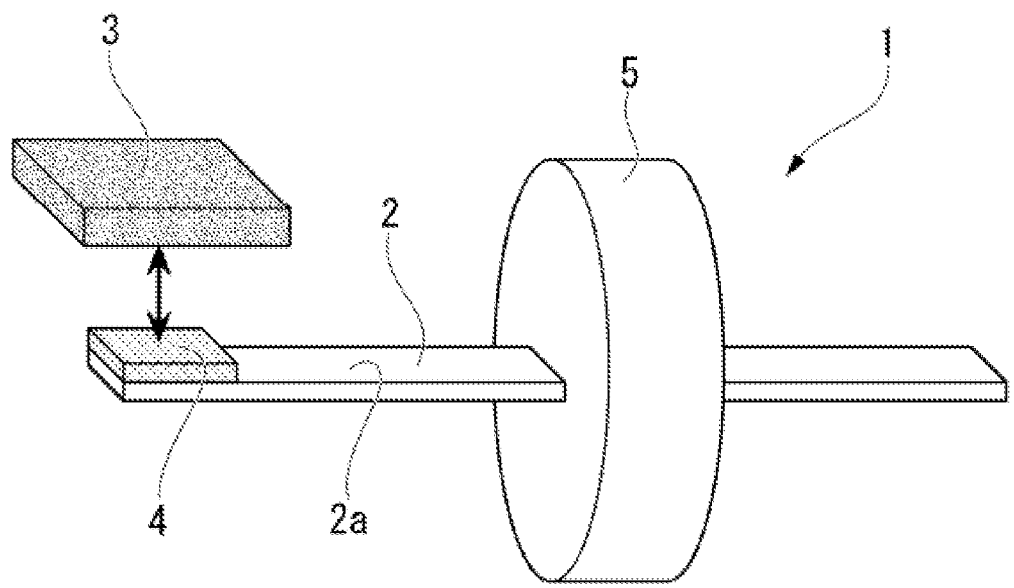
FIG. 2 is a perspective view showing a part of a manufacturing process of the wiring structure according to the first embodiment.

FIG. 2 shows a step of connecting the permanent magnet 3 to the relay piece 4 after the relay piece 4 is connected to the terminal portion (the conductive portion) of the flexible printed wiring board 2. The permanent magnet 3 is fixed by magnetic attraction to the relay piece 4 connected to the flexible printed wiring board 2. In the embodiment, a conductive adhesive is provided between the permanent magnet 3 and the relay piece 4. Thus, the permanent magnet 3 and the relay piece 4 are fixed together by the magnetic force of the permanent magnet 3 and the adhesive strength of the adhesive.

The other end portion of the terminal portion can be connected to a circuit board having a resistance detecting circuit or the like (not shown). In the embodiment, the longitudinally midway portion of the flexible printed wiring board 2 has integrally formed thereon a grommet 5 that serves as a sealing member. In installing the wiring structure 1 on a mechanical device such as a speed reducer, the grommet 5 is fitted into a through-hole formed in a casing of the mechanical device. In the through-hole, the grommet 5 seals between the casing and the flexible printed wiring board 2. The flexible printed wiring board 2 extends through the through-hole and is present both inside and outside the mechanical device. In other words, the grommet 5 seals between a lubricant-filled space (inside of the mechanical device) in which the permanent magnet 3 is disposed and a circuit board-containing space (detection space, outside of the mechanical device) in which the circuit board is disposed.

Advantageous Effects of First Embodiment

The wiring structure 1 of the embodiment includes the permanent magnet 3 having electrical conductivity, a flexible printed wiring board 2 (wiring) including the conductive portion, and the relay piece 4 formed of a metal magnetic material, the relay piece 4 being connected to the conductive portion of the flexible printed wiring board 2 and having the permanent magnet 3 fixed thereto by magnetic attraction. Therefore, the permanent magnet 3 can be fixed to the relay piece 4 by magnetic attraction for connection between the conductive portion of the flexible printed wiring board 2 (wiring) and the permanent magnet 3. There is no need of a cutting process for forming a screw hole or the like in the permanent magnet 3. Accordingly, with the wiring structure 1 of the embodiment, it is possible to easily connect between the conductive portion of the flexible printed wiring board 2 (wiring) and the permanent magnet 3 without increase of the size of the connection portion.

The wiring for electrically connecting between the permanent magnet 3 and the circuit board may be formed of a coated conductive wire having a circular or rectangular cross section, in place of the flexible printed wiring board 2. However, when the flexible printed wiring board 2 is used as the wiring for electrically connecting between the permanent magnet 3 and the circuit board, as in the wiring structure 1 of the embodiment, the wiring can run freely even in a small installation space, and the wiring form can be stable. Since the flexible printed wiring board 2 has a flat surface, the relay piece 4 can be stably supported on the flat surface of the flexible printed wiring board 2.

In the wiring structure 1 of the embodiment, the relay piece 4 and the permanent magnet 3 are connected together also with the conductive adhesive. Therefore, the permanent magnet 3 can be fixed firmly to the relay piece 4 by the adhesive strength of the conductive adhesive, in addition to the attractive force of the permanent magnet 3. In actually connecting the permanent magnet 3 to the relay piece 4, it is necessary only to previously apply the conductive adhesive to at least one of the relay piece 4 or the permanent magnet 3 and allow the permanent magnet 3 to be attached to the relay piece 4 by magnetic attraction. Thus, there is no complexity in manufacturing the wiring structure 1.

In the wiring structure 1 of the embodiment, the relay piece 4 has a flat surface. The permanent magnet 3 is fixed to the flat surface of the relay piece 4 by magnetic attraction. Therefore, this configuration stabilizes the electrical connection and mechanical fixation between the relay piece 4 and the permanent magnet 3.

Even when the relay piece 4 and the conductive portion of the flexible printed wiring board 2 (wiring) are formed of such a material or have such structure as to be less suited for connection by solder, the relay piece 4 can be connected to the conductive portion of the flexible printed wiring board 2 (wiring) with the conductive adhesive, thereby stabilizing the connection between the relay piece 4 and the conductive portion of the flexible printed wiring board 2 (wiring) in a conductive manner.

Second Embodiment

Figure 3:
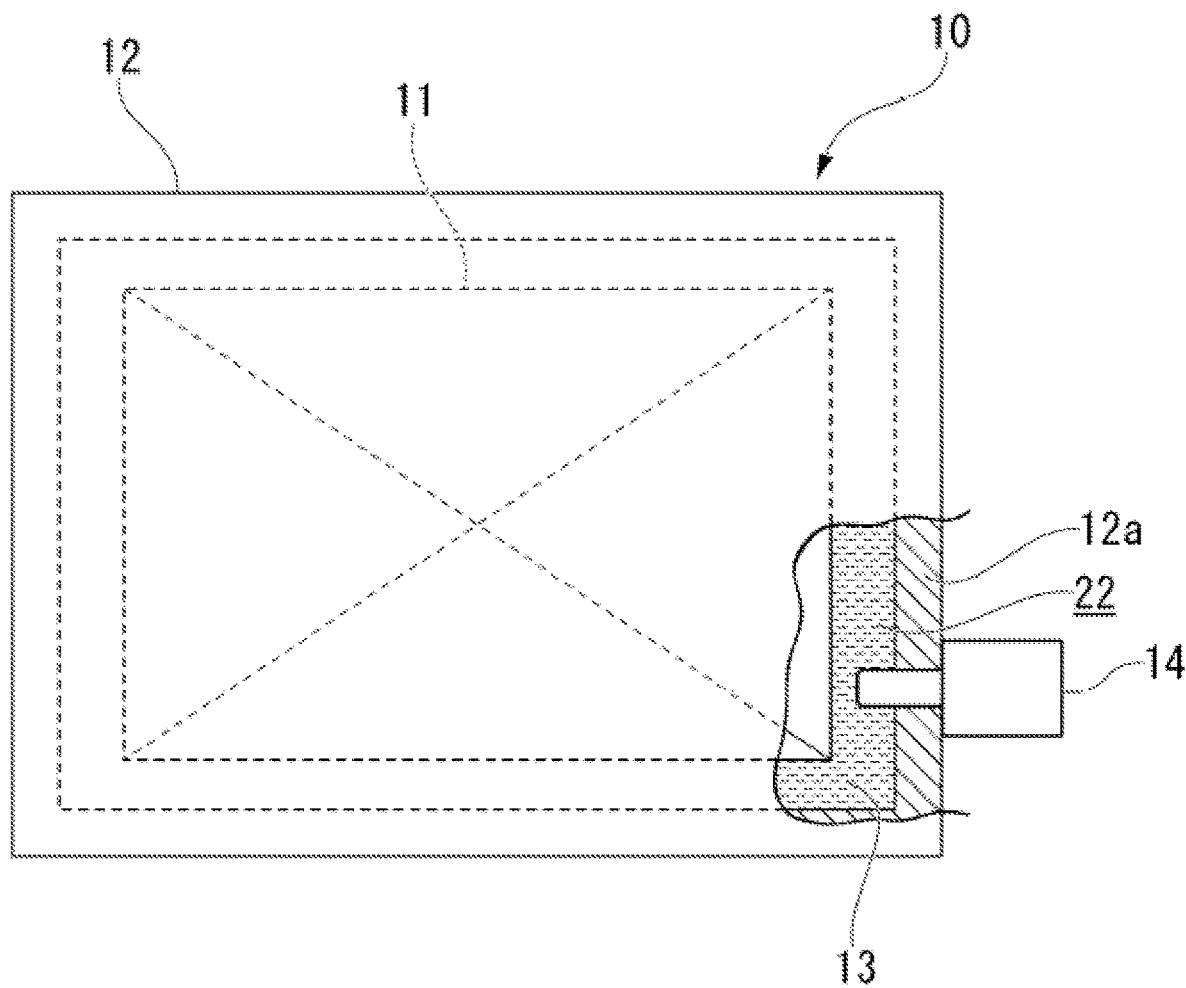
FIG. 3 is a partially sectional side view showing a speed reducer having mounted thereto a conductive particle detecting device according to a second embodiment.

FIG. 3 is a partially sectional side view showing a speed reducer 10 according to a second embodiment. The speed reducer 10 includes: a speed reducing mechanism unit 11 for decelerating input rotation to a predetermined reduction ratio; and a casing 12 that houses the speed reducing mechanism unit 11. The inner space within the casing 12 is filled with a lubricant 13 for lubricating the speed reducing mechanism unit 11 and other mechanical contact parts. A conductive particle detecting device 14 is mounted to a wall 12a of the casing 12. The conductive particle detecting device 14 detects conductive particles such as metal powder mixing into the lubricant 13.

Figure 4:
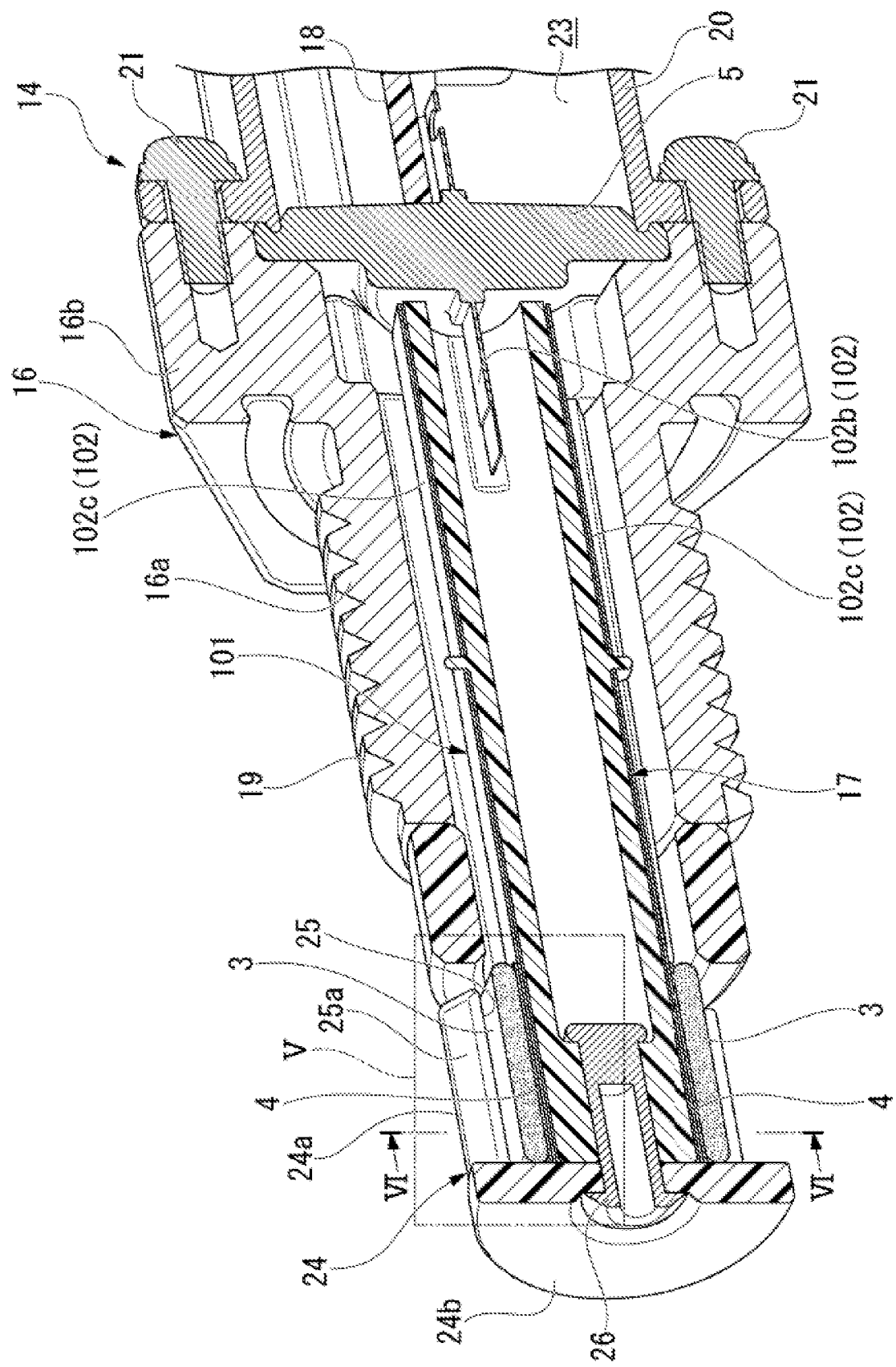
FIG. 4 is a partial sectional perspective view showing the conductive particle detecting device according to the second embodiment.
Figure 5:
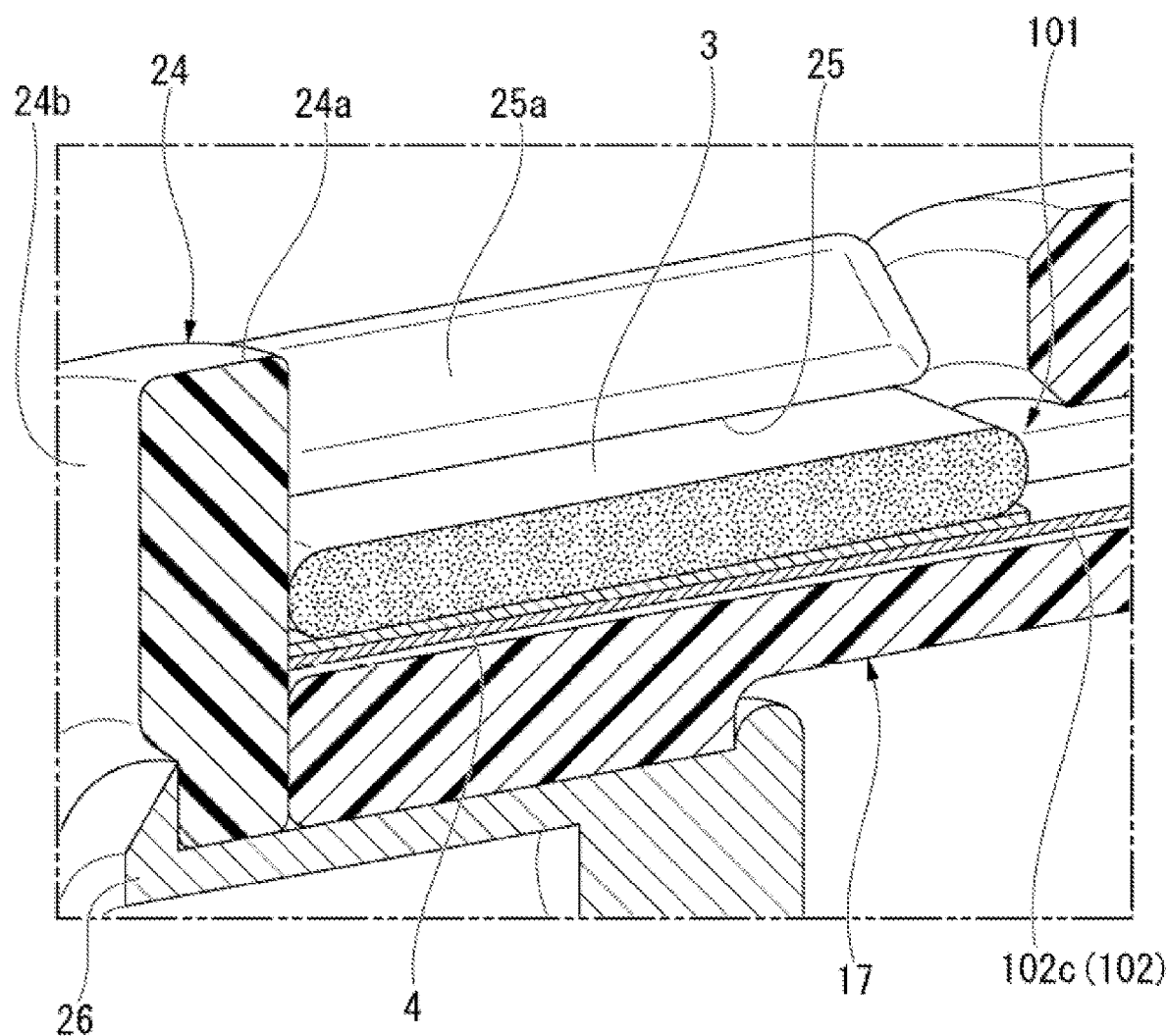
FIG. 5 is a partial sectional perspective view showing, in an enlarged scale, the V portion in FIG. 4 of the conductive particle detecting device according to the second embodiment.
Figure 6:
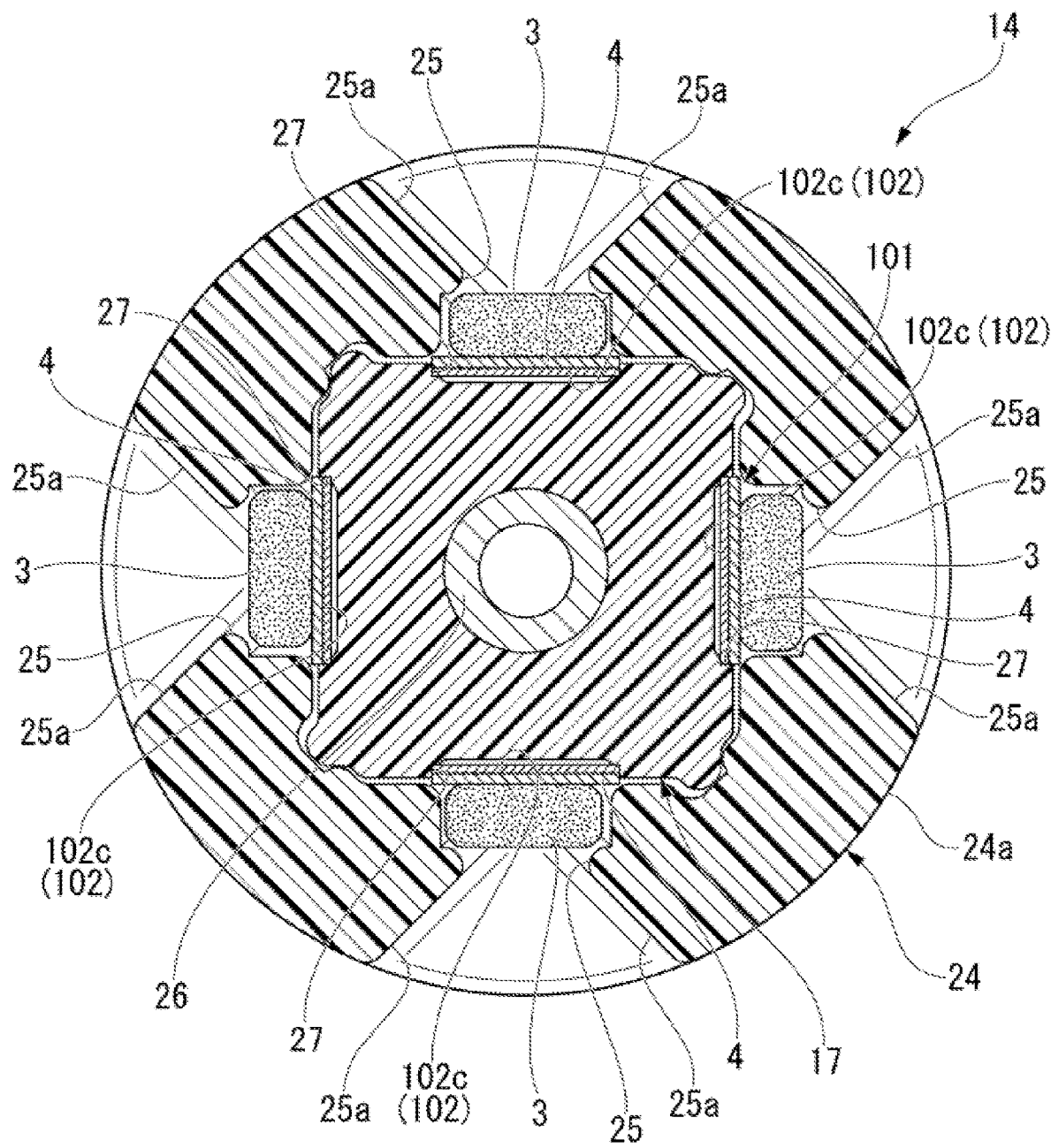
FIG. 6 is a sectional view showing the conductive particle detecting device according to the second embodiment cut along the line VI-VI in FIG. 4.

FIG. 4 is a perspective view showing a part of the conductive particle detecting device 14 longitudinally sectioned along the longitudinal direction. FIG. 5 is an enlarged view of the portion V of FIG. 4. FIG. 6 is a sectional view along a line VI-VI in FIG. 4. The conductive particle detecting device 14 includes a device body 16 having a substantially tubular shape, a support block 17 fixed to the inside of the device body 16, and a flexible printed wiring board 102 (wiring) supported by the support block 17. The conductive particle detecting device 14 includes: four permanent magnets 3 connected via the relay pieces 4 to one end portion of the flexible printed wiring board 102 in the longitudinal direction; and a detecting circuit board 18 connected to the other end portion of the flexible printed wiring board 102 in the longitudinal direction. The permanent magnets 3, the flexible printed wiring board 102, and the relay pieces 4 constitute a wiring structure 101 according to the embodiment.

The device body 16 is mounted to the casing 12 (see FIG. 3) of the speed reducer 10. The wall 12a of the casing 12 has a screw hole penetrating the wall 12a. The device body 16 is formed of, for example, a metal. The device body 16 includes a fixed tube 16a having a cylindrical shape and a flange portion 16b. The fixed tube 16a is fastened into the screw hole formed in the wall 12a. Thus, the device body 16 is mounted to the casing 12 in such a manner as to penetrate the wall 12a. The flange portion 16b is integrated with the other end portion of the fixed tube 16a (the end portion positioned outside the casing 12).

A male thread 19 is formed in the outer circumferential surface of the fixed tube 16a. The male thread 19 is fastened into the screw hole in the wall 12a. A device cover 20 having a bottomed tubular shape is provided outside the flange portion 16b. The device cover 20 is fixed with bolts 21 (fastening members) to an outside end surface of the flange portion 16b (the end surface facing toward the opposite side to the casing 12). A grommet 5 (sealing member) shaped like a disc seals between the device cover 20 and the flange portion 16b. The grommet 5 is integrated with a part of an insulating layer 102a (see FIG. 7) of the flexible printed wiring board 102. The flexible printed wiring board 102 is integrated with the grommet 5 so as to penetrate the grommet 5 in the thickness direction thereof.

The detecting circuit board 18 is mounted to the outside end surface of the grommet 5 (the end surface facing toward the opposite side to the casing 12). The detecting circuit board 18 is covered by the device cover 20. The grommet 5 is fixed to the device cover 20 and the flange portion 16b, with the peripheral edge of the grommet 5 nipped between the device cover 20 and the flange portion 16b. The grommet 5 seals between the lubricant-filled space 22 (see FIG. 3) inside the casing 12 and a detection space 23 (the space inside the device cover 20) in which the detecting circuit board 18 is disposed.

The support block 17 is formed of a resin material and shaped like a hollow quadrangular prism. The other end portion (hereinafter referred to as "the proximal portion") of the support block 17 in the longitudinal direction is fixed to the inside of the device body 16. The support block 17 is positioned along the axial direction of the fixed tube 16a. One end portion (hereinafter referred to as "the distal end portion") of the support block 17 in the longitudinal direction projects out of the fixed tube 16a of the device body 16 (to the inside of the casing 12).

The outer peripheral surface and the distal end surface of the distal end portion of the support block 17 are covered by a detecting unit cover 24 having a bottomed tubular shape. The detecting unit cover 24 is integrally formed of a resin material. The detecting unit cover 24 includes a peripheral wall 24a and an end wall 24b. The peripheral wall 24a has four detection windows 25, and the end wall 24b closes the axial end portion of the peripheral wall 24a. The four detection windows 25 of the peripheral wall 24a are arranged at regular intervals and spaced apart from each other by about 90° in the outer periphery of the peripheral wall 24a. Each of the detection windows 25 has a substantially rectangular shape in front view. Of the edges constituting each detection window 25, those on both sides along the circumferential direction of the peripheral wall 24a are formed in tapered surfaces 25a. The tapered surfaces 25a are formed such that the opening area of the detection window 25 increases gradually radially outward.

The end wall 24b of the detecting unit cover 24 is riveted to the distal end surface of the support block 17. The sign 26 in the drawing denotes a rivet for fixing the detecting unit cover 24 to the support block 17.

Figure 7:
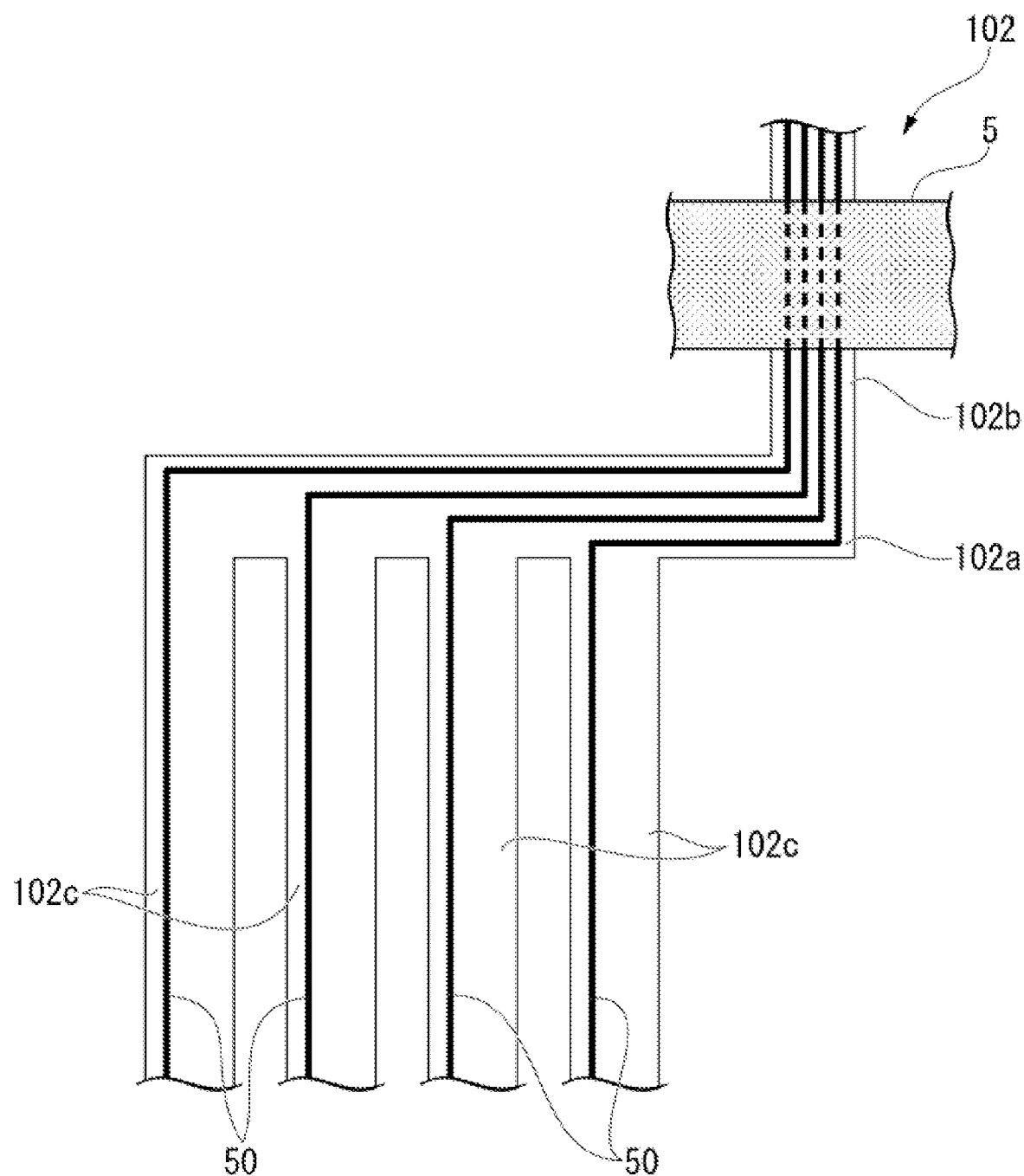
FIG. 7 is a plan view showing a flexible printed wiring board used in the conductive particle detecting device according to the second embodiment.

FIG. 7 is a plan view showing the flexible printed wiring board 102. As shown in FIG. 7, the flexible printed wiring board 102 according to the embodiment includes a base portion 102b and four branch portions 102c branched from the base portion 102b. The base portion 102b penetrates the grommet 5 in the thickness direction thereof. The flexible printed wiring board 102 includes conductive portions 50 extending from the base portion 102b to the distal end portions of the branch portions 102c. The other end portion (the terminal portion) of the conductive portions 50 is positioned outside the casing 12 and connected to the detecting circuit board 18. Each of the four branch portions 102c branched from the base portion 102b is positioned along associated one of the four surfaces on the outer periphery of the support block 17. Support grooves 27 (see FIG. 6) are formed in the four surfaces on the outer periphery of the support block 17 so as to extend along the longitudinal direction of the support block 17. In each surface of the support block 17, the branch portion 102c is supported in the support groove 27.

At the distal end portion of each of the branch portions 102c, one end portion of the conductive portion 50 is connected with the relay piece 4. The relay piece 4 is formed of a metal magnetic material and has a substantially rectangular shape. The relay piece 4 is connected to the conductive portion 50 with a conductive adhesive or by soldering. On the distal end side of the support block 17, each relay piece 4 is supported in the associated support groove 27 along with the branch portion 102c.

The surface of each relay piece 4 facing the opposite side to the support block 17 (hereinafter referred to as "the surface") is formed flat. The surface of each relay piece 4 has the associated permanent magnet 3 fixed thereto by magnetic attraction. In the embodiment, it is also possible that the permanent magnet 3 is fixed to the relay piece 4 by combined use of a conductive adhesive.

After the relay piece 4 and the permanent magnet 3 are mounted to each surface on the outer periphery of the support block 17, the detecting unit cover 24 is mounted to the distal end portion of the support block 17. The detecting unit cover 24 is positioned such that each of the four permanent magnets 3 is positioned on the inner side of the associated one of the four detection windows 25 (on the inner side in the radial direction of the peripheral wall 24a). In this state, the detecting unit cover 24 is riveted to the distal end surface of the support block 17. At this time, the end surface of the peripheral wall 24a of the detecting unit cover 24 (the end surface on the opposite side to the end wall 24b) abuts against the end surface of the fixed tube 16a of the device body 16.

The distal end portion of the conductive particle detecting device 14 is inserted into the casing 12 through the screw hole in the wall 12a. In this state, the fixed tube 16a of the conductive particle detecting device 14 is fastened into the screw hole. Thus, the conductive particle detecting device 14 is fixed to the casing 12. The lubricant 13 is then filled into the casing 12, and the plurality of permanent magnets 3 and the detecting unit cover 24 are immersed in the lubricant 13.

The detecting circuit board 18 includes a resistance detecting circuit. The resistance detecting circuit detects the electrical resistance between the plurality of permanent magnets 3 arranged adjacent to each other on the outer periphery of the support block 17. As shown in FIG. 6, the plurality of permanent magnets 3 are spaced apart from each other. Therefore, in the initial state in which the permanent magnets 3 are immersed in the lubricant 13, the resistance value between adjacent permanent magnets 3 is infinite. After that, when a large amount of conductive particles (such as metal powder) mixes into the lubricant 13 as the speed reducer 10 is used, the conductive particles in the lubricant 13 are attracted by the plurality of permanent magnets 3 of the conductive particle detecting device 14. The conductive particles attracted are moved through the detection windows 25 of the detecting unit cover 24 and adhered onto the surfaces of the permanent magnets 3. Also, the conductive particles attracted are adhered onto the outer peripheral surface of the detecting unit cover 24 by the magnetic force of the permanent magnets 3.

As a larger amount of conductive particles mix into the lubricant 13, a larger amount of conductive particles are also adhered onto the outer peripheral surface of the detecting unit cover 24. When the amount of conductive particles adhered exceeds a certain amount, the resistance value between adjacent ones of the permanent magnets 3 falls below a preset value. The detecting circuit board 18 detects that the resistance value has fallen below the preset value. The detecting circuit board 18 is connected to a display device or an alarm device via a controller. Through the display device or the alarm device, an operator and the like can determine that the amount of conductive particles in the speed reducer 10 has exceeded the preset amount.

Advantageous Effects of Second Embodiment

As described above, the conductive particle detecting device 14 of the embodiment includes: the plurality of permanent magnets 3 having electrical conductivity and spaced apart from each other; the detecting circuit board 18; the flexible printed wiring board 102 connecting between the detecting circuit board 18 and the permanent magnets 3; and the relay pieces 4 made of a metal magnetic material, the relay pieces 4 being connected to conductive portions 50 of the flexible printed wiring board 102 on the permanent magnet 3 side and having the permanent magnets 3 attached thereto by magnetic attraction. In the conductive particle detecting device 14 of the embodiment, the permanent magnets 3 having electrical conductivity can be fixed to the relay pieces 4 by magnetic attraction. Therefore, in connecting the conductive portions 50 of the flexible printed wiring board 102 and the permanent magnets 3 having electrical conductivity, there is no need of a cutting process for forming a screw hole or the like in the permanent magnets 3. Accordingly, with the conductive particle detecting device 14 of the embodiment, it is possible to easily connect the conductive portions 50 of the flexible printed wiring board 102 and the permanent magnets 3 having electrical conductivity without increase of the size of the connection portion.

In the conductive particle detecting device 14 of the embodiment, when the conductive portions 50 of the flexible printed wiring board 102 and the relay pieces 4 are connected by solder, the relay pieces 4 made of a metal magnetic material can be firmly fixed to the conductive portions 50 of the flexible printed wiring board 102.

In the conductive particle detecting device 14 of the embodiment, even when the relay pieces 4 and the conductive portions 50 of the flexible printed wiring board 102 are formed of such a material or have such structure as to be less suited for connection by solder, the conductive portions 50 of the flexible printed wiring board 102 and the relay pieces 4 can be connected by the conductive adhesive, thereby stabilizing the fixation of the relay pieces 4 to the conductive portions 50 of the flexible printed wiring board 102 in a conductive manner.

The conductive particle detecting device 14 of the embodiment uses the flexible printed wiring board 102 as wiring for electrically connecting the permanent magnets 3 and the detecting circuit board 18. Therefore, the wiring can run freely even in a small installation space within the conductive particle detecting device 14, and the wiring form can be stable.

In the conductive particle detecting device 14 of the embodiment, the grommet 5 (sealing member) is integrated with the flexible printed wiring board 102. The grommet seals between the lubricant-filled space 22 in the speed reducer 10 filled with the lubricant 13 and the detection space 23 in which the detecting circuit board 18 is disposed. This simple structure facilitates manufacturing and assembling and also securely prevents the lubricant 13 from entering the detection space 23.

The present disclosure is not limited to the above-described embodiments and can be modified in a variety of designs without deviating from the spirit of the present disclosure.

What is claimed is:

1. A wiring structure comprising:
   a plurality of permanent magnets having electrical conductivity and spaced apart from each other;
   a detecting circuit board for detecting conductive particles attracted between adjacent ones of the plurality of permanent magnets, based on electrical resistance between the adjacent ones of the plurality of permanent magnets;
   a wiring having a conductive portion;
   a plurality of relay pieces made of a metal magnetic material, the plurality of relay pieces being connected to the conductive portion, the plurality of permanent magnets being fixed to the plurality of relay pieces by magnetic attraction, and
   a sealing member sealing between a lubricant-filled space containing the plurality of permanent magnets and filled with a lubricant and a detection space containing the detecting circuit board,
   wherein the wiring is formed of a flexible printed wiring board, and
   wherein the sealing member is integrated with the flexible printed wiring board.

2. The wiring structure of claim 1, wherein the plurality of relay pieces and the plurality of permanent magnets are connected by a conductive adhesive.

3. A conductive particle detecting device, comprising:
   a plurality of permanent magnets having electrical conductivity and spaced apart from each other;
   a detecting circuit board for detecting conductive particles attracted between adjacent ones of the plurality of permanent magnets, based on electrical resistance between the adjacent ones of the plurality of permanent magnets;
   a flexible printed wiring board electrically connecting the detecting circuit board and the plurality of permanent magnets; and
   a plurality of relay pieces connected to conductive portions of the flexible printed wiring board,
   wherein the plurality of relay pieces are made of a metal magnetic material, and
   wherein the plurality of permanent magnets are fixed to the plurality of relay pieces, respectively, by magnetic attraction,
   a sealing member sealing between a lubricant-filled space containing the plurality of permanent magnets and filled with a lubricant and a detection space containing the detecting circuit board,
   wherein the sealing member is integrated with the flexible printed wiring board.

4. The conductive particle detecting device of claim 3, wherein the conductive portions and the plurality of relay pieces are connected by solder.

5. The conductive particle detecting device of claim 3, wherein the conductive portions and the plurality of relay pieces are connected by a conductive adhesive.

6. A speed reducer comprising:
   a speed reducing mechanism unit for reducing a speed of rotation input thereto;
   a casing containing the speed reducing mechanism unit; and
   a conductive particle detecting device for detecting conductive particles mixing into a lubricant in the casing,
   wherein the conductive particle detecting device includes:
   a plurality of permanent magnets having electrical conductivity and spaced apart from each other within the casing;
   a detecting circuit board for detecting conductive particles attracted between adjacent ones of the plurality of permanent magnets, based on electrical resistance between the adjacent ones of the plurality of permanent magnets;
   a flexible printed wiring board electrically connecting the detecting circuit board and the plurality of permanent magnets; and
   a plurality of relay pieces connected to conductive portions of the flexible printed wiring board,
   wherein the plurality of relay pieces are made of a metal magnetic material, and
   wherein the plurality of permanent magnets are fixed to the plurality of relay pieces, respectively, by magnetic attraction
   a sealing member sealing between a lubricant-filled space containing the plurality of permanent magnets and filled with a lubricant and a detection space containing the detecting circuit board,
   wherein the sealing member is integrated with the flexible printed wiring board.

* * * * *